US011123414B2

(12) United States Patent
Glen et al.

(10) Patent No.: US 11,123,414 B2
(45) Date of Patent: Sep. 21, 2021

(54) NON-CARCINOGENIC CREAM FOR DELIVERY OF ACTIVE INGREDIENT INTO THE DERMIS

(71) Applicant: PRODUITS NATURASENSE INC., Mont-Tremblant (CA)

(72) Inventors: Samuel Glen, Kelowna (CA); Barbara J. Johnston, Kelowna (CA); Lynda Therrien Berthiaume, Mont-Tremblant (CA); Molly Sharma, Kelowna (CA)

(*) Notice: Subject to any disclaimer, the term of this patent is extended or adjusted under 35 U.S.C. 154(b) by 140 days.

(21) Appl. No.: 15/853,562

(22) Filed: Dec. 22, 2017

(65) Prior Publication Data

US 2019/0192642 A1    Jun. 27, 2019

(51) Int. Cl.

| | |
|---|---|
| A61K 38/54 | (2006.01) |
| A61K 47/26 | (2006.01) |
| A61K 36/45 | (2006.01) |
| A61K 36/88 | (2006.01) |
| A61K 36/30 | (2006.01) |
| A61K 36/28 | (2006.01) |
| A61K 36/81 | (2006.01) |
| A61K 36/185 | (2006.01) |
| A61K 33/28 | (2006.01) |
| A61K 36/23 | (2006.01) |
| A61K 36/714 | (2006.01) |
| A61K 33/04 | (2006.01) |
| A61K 47/44 | (2017.01) |
| A61K 47/10 | (2017.01) |
| A61K 47/12 | (2006.01) |
| A61K 36/75 | (2006.01) |
| A61K 9/06 | (2006.01) |
| A61K 9/00 | (2006.01) |
| A61K 41/00 | (2020.01) |
| A61K 47/42 | (2017.01) |
| A61K 36/886 | (2006.01) |
| A61K 47/14 | (2017.01) |

(52) U.S. Cl.
CPC ............ *A61K 38/54* (2013.01); *A61K 9/0014* (2013.01); *A61K 9/06* (2013.01); *A61K 33/04* (2013.01); *A61K 33/28* (2013.01); *A61K 36/185* (2013.01); *A61K 36/23* (2013.01); *A61K 36/28* (2013.01); *A61K 36/30* (2013.01); *A61K 36/45* (2013.01); *A61K 36/714* (2013.01); *A61K 36/75* (2013.01); *A61K 36/81* (2013.01); *A61K 36/88* (2013.01); *A61K 36/886* (2013.01); *A61K 41/00* (2013.01); *A61K 41/0004* (2013.01); *A61K 47/10* (2013.01); *A61K 47/12* (2013.01); *A61K 47/14* (2013.01); *A61K 47/26* (2013.01); *A61K 47/42* (2013.01); *A61K 47/44* (2013.01)

(58) Field of Classification Search
None
See application file for complete search history.

(56) References Cited

U.S. PATENT DOCUMENTS

| | | | | |
|---|---|---|---|---|
| 5,795,573 A | * | 8/1998 | Paradise | A61K 36/22 424/125 |
| 2006/0165812 A1 | * | 7/2006 | Charron | A61K 33/00 424/600 |
| 2010/0316737 A1 | * | 12/2010 | Farrington | A61K 33/00 424/725 |
| 2011/0280854 A1 | * | 11/2011 | Fallon | A61K 38/465 424/94.2 |
| 2014/0155342 A1 | * | 6/2014 | Irianni | A61K 9/7061 514/33 |
| 2018/0125980 A1 | * | 5/2018 | Finley | A61K 47/22 |

OTHER PUBLICATIONS

Olajubu, Int. J. Curr. Microbiol. App. Sci., 3(8):418-425 (2014) (Year: 2014).*
Che et al., Molecules, 18:5125-5141 (2013) (Year: 2013).*
Sankar et al., Indian. J. Tradit. Knowle., 16(1):158-163 (2017) (Year: 2017).*
Boericke, http://homeoint.org/books/boericmm/m/merc-i-r.htm (2017), Accessed Oct. 29, 2019 (Year: 2017).*
Colalto et al., Drug Metab. Toxicol., 3(2):1000e105 (2012) (Year: 2012).*
Johnson, https://www.111heavenscent.com/tinctures-v-essential-oils (2016), Accessed Aug. 25, 2020). (Year: 2016).*

* cited by examiner

*Primary Examiner* — Thomas J. Visone
(74) *Attorney, Agent, or Firm* — France Cote

(57) ABSTRACT

The present document describes a non-carcinogenic cream for delivery of active ingredients in the dermis of a patient, which comprises a synergistic combination of
  about 10 to 25% of oil
  about 10 to 25% of emulsifier
  about 1 to 12% of preservative
  about 45 to 80% of water, aloe water or hamamelis water; and
  about 1 to 25% of at least one homeopathic active ingredient chosen from pancreatinum, ruta graveolens, ledum palustre, colchicum autumnale, symphytum officinalis, salix alba, harpagophytum, bryonia, capsicum, rhododendron, benzoic acid, salicilicum acid, arnica montana, atropa belladonna, achillea millefolium, hamamelis, agaricus, aesculus, mercurius solubilis, mercurius iodatus, conium maculatum, echinacea angustifolia, echinacea purpurea, scrofularia nosada, pulsatilla, aconitum napellus, hypericum perforatum, bellis perennis, matricaria chamomilla, ranunculus, phytolacca decandra, dulcamara solanum, kalmia, actea racemosa, spigelia, gnaphalium, calendula officinalis, hepar sulphuris, somniferrum, calcarea fluorica, thiosinaminum, hydrastis, arctium lappa, gallium aparine, urtica urens, aloe, graphite, petroleum or a synergistic combination thereof.

3 Claims, No Drawings

NON-CARCINOGENIC CREAM FOR DELIVERY OF ACTIVE INGREDIENT INTO THE DERMIS

BACKGROUND (a) Field

The subject matter disclosed generally relates to a non-carcinogenic cream for delivery of active ingredients into the dermis of a patient for pain related to joint, lymphatic and blood circulation, nerve and skin.

(b) Related Prior Art

Many pharmaceutical analgesic topical compositions for treating muscular cramps, soreness and pain contain irritants, counter-irritants and toxic ingredients that are mostly carcinogenic and mask pain instead of alleviating it. These compositions irritate the skin and do not treat all the symptoms, causes pain and side effects and/or increase the risk of developing cancer.

Homeopathy is an ancient healing art and forms a vital part of medical therapy. The practice of homeopathy is widespread, particularly in eastern cultures and many European countries. Homeopathic medicine teaches the use of natural based remedies and, as such, provides an alternative to traditional allopathic medicine which relies heavily on the use of petrochemical based pharmaceuticals. There has been a large increase in interest in homeopathic medicine in the United States in recent years due, in large part, to a growing disenchantment with allopathic medications and the complications and side effects arising from their use. Frequently, the administration of allopathic medications results in serious side effects more deleterious to the patient than the basic condition being treated. Today, more and more individuals are looking for a gentler, safer path to good health free of the risks and side effects associated with traditional allopathic medicines.

In order to relieve pain in many inflammatory injuries or diseases it is desirable to promote healing, improve circulation to tissues nerves, provide anti-inflammatory activity, while alleviating pain instead of masking it. Many injuries have a multiplicity of symptoms which require a cocktail of ingredients working together in order to provide relief.

Furthermore, it is desirable to obtain deep penetration of the active ingredients so as to act in the dermis to provide the proper response to cause healing of the injury and/or inflammation.

It is further desirable to provide an analgesic which does not rely upon counter-irritants that act by causing a superficial inflammation on the skin, which numbs the sensation of pain perceived by the sensory organ and results in only masking the pain instead of alleviating it.

It is further desirable to relax soft tissues, vasodilate blood vessels which are vasoconstricted so as to allow blood to flow normally, returning nutrients and oxygen to areas to promote healing. It is also desirable to release nerves which have been entrapped by hypercontraction of muscle tissue.

U.S. Pat. No. 5,162,037 to Whitson-Fischman discloses a method for treating pathogenic conditions of the body by preparing a homeopathic mixture of at least one herb or herbal extract which exhibits therapeutic property and add a magnetically permeable substance to the mixture, magnetizing the resulting mixture in a magnetic field during delivery to impart a substantially unipolar magnetic charge on said mixture; and administering the magnetized mixture through one or more specific acupuncture points of the body which are associated with producing a desired response to the particular condition being treated.

U.S. Pat. No. 5,795,573 to Paradise discloses homeopathic topical anti-inflammatory and pain relieving compositions. Although the compositions active ingredients include homeopathic extracts from Arnica Montana, Rhus toxicodendron and Aesculus hippocastanum and belladonna, they also include carcinogenic ingredients such as PEG, PPG, ethoxydiglycol, paraben, isopropyl myristate and Dowicil 200.

Finally, it is highly desirable to have a non-carcinogenic cream for the treatment of pain.

SUMMARY

It is an object of the present disclosure to provide a non-carcinogenic cream for delivery of active ingredients in the dermis of a patient for pain related to joint, lymphatic and blood circulation, nerve and skin.

According to an embodiment, there is provided a non-carcinogenic cream for delivery of active ingredients in the dermis of a patient, comprises a synergistic combination of
- about 10 to 25% of oil
- about 10 to 25 of emulsifier
- about 1 to 12% of preservative
- about 45 to 80% of water, aloe water or hamamelis water, and
- about 1 to 25% of at least one homeopathic active ingredient chosen from pancreatinum, ruta graveolens, ledum palustre, colchicum autumnale, symphytum officinalis, salix alba, harpagophytum, bryonia, capsicum, rhododendron, benzoic acid, salicilicum acid, arnica montana, atropa belladonna, achillea millefolium, hamamelis, agaricus, aesculus, mercurius solubilis, mercurius iodatus, conium maculatum, echinacea angustifolia, echinacea purpurea, scrofularia nosada, pulsatilla, aconitum napellus, hypericum perforatum, bellis perennis, matricaria chamomilla, ranunculus, phytolacca decandra, dulcamara solanum, kalmia, actea racemosa, spigelia, gnaphalium, calendula officinalis, hepar sulphuris, somniferrum, calcarea fluorica, thiosinaminum, hydrastis, arctium lappa, gallium aparine, urtica urens, aloe, graphite, petroleum or a synergistic combination thereof.

The oil is chosen from emu oil, olive oil, argan nut oil, sunflower/safflower oil, coconut oil, castor oil, avocado oil, jojoba oil, lavender oil, grape seed oil, poppy seed oil, sunflower oil or wheat germ oil.

The emulsifier is chosen from oleyl oleate, cetearyl alcohol, cetearyl wheat straw glucosides, glyceryl stearate, sodium stearoyl lactylate, cetearyl olivate, sorbitan olivate, propylene glycol esters (pgms), borax with bees wax, bees wax, BTMS 25%, carbomer, emulsifying wax-NF, lecithin, stearate, silky emulsifying wax, stearyl alcohol NF, shea butter, cocoa butter, coconut oil or stearic acid.

The preservative is chosen from a combination of glucose, glucose oxidase and lactoperoxidase (Biovert™ enzymes), a combination of benzyl alcohol, salicylic acid, glycerin and sorbic acid (Geoguard™ ECT), polylysine, natamycin, nisin, isothiazolinones, benzoic acid—sodium benzoate, sorbic acid—potassium sorbate, levulinic acid, anisic acid, rosemary oil extract, grapefruit seed extract, T-50 vitamin E oil, jermaben 11, or jermaben 11-E.

The non-carcinogenic cream for improving joint conditions contains at least one homeopathic active ingredient chosen from pancreatinum, ruta graveolens, ledum palustre, colchicum autumnale, symphytum officinalis, salix alba, harpagophytum, bryonia, capsicum, rhododendron, benzoic acid, salicilicum acid or a synergistic combination thereof.

The non-carcinogenic cream for improving blood circulation contains at least one homeopathic active ingredient chosen from arnica montana, atropa belladonna, achillea millefolium, hamamelis, agaricus, aesculus or a synergistic combination thereof.

The non-carcinogenic cream for improving lymphatic circulation contains at least one homeopathic active ingredient chosen from mercurius solubilis, mercurius iodatus, conium maculatum, echinacea angustifolia, echinacea purpurea, gallium aparine, phytolacca decandra, scrofularia nosada, pulsatilla or a synergistic combination thereof.

The non-carcinogenic cream for improving sensitive nerves contains at least one homeopathic active ingredient chosen from aconitum napellus, hypericum perforatum, bellis perennis, matricaria chamomilla, ranunculus, phytolacca decandra, dulcamara solanum, kalmia, actea racemosa, spigelia, gnaphalium or a synergistic combination thereof.

The non-carcinogenic cream for reducing scars and/or keloids of the skin contains at least one homeopathic active ingredient chosen from pancreatinum, calendula officinalis, hepar sulphuris, somniferrum, calcarea fluorica, thiosinaminum, hydrastis, arctium lappa, gallium aparine, urtica urens, aloe, graphite, petroleum or a synergistic combination thereof.

The preferred non-carcinogenic cream comprises
about 14.7% of oil;
about 12.8% of emulsifier;
about 1.05% of preservative; and
about 65.67% of water; and
about 4.78% the homeopathic active ingredient comprises at least pancreatinum, ruta graveolens, ledum palustre, colchicum autumnale, symphytum officinalis, arnica montana, atropa belladonna, achillea millefolium, hamamelis, mercurius solubilis, mercurius iodatus, conium maculatum, echinacea angustifolia, echinacea purpurea, aconitum napellus, hypericum perforatum, bellis perennis, matricaria chamomilla, calendula officinalis and hepar sulphuris.

According to another embodiment, there is provided a non-carcinogenic cream for delivery of active ingredients in the dermis of a patient comprises a synergistic combination of
about 10 to 25% of oil
about 10 to 250f emulsifier
about 1 to 12% of preservative
about 45 to 80% of water, aloe water or hamamelis water, and
about 1 to 25% of a synergistic combination of at least five homeopathic active ingredients comprising
from at least one of aconitum napellus, hypericum perforatum, bellis a first ingredient chosen from at least one of ruta graveolens, ledum palustre, colchicum autumnale or symphytum officinalis;
a second ingredient chosen from at least one of arnica montana, atropa belladonna, achillea millefolium or hamamelis;
a third ingredient chosen from at least one of mercurius solubilis, mercurius iodatus, conium maculatum, echinacea angustifolia or echinacea purpurea;
a fourth ingredient chosen from at least one perennis, matricaria chamomilla, gallium aparine, phytolacca decandra, scrofularia nosada, or pulsatilla;
a fifth ingredient chosen from at least one of pancreatinum, calendula officinalis, hepar sulphuris, somniferrum, calcarea fluorica, thiosinaminum, hydrastis, arctium lappa, gallium aparine, urtica urens, aloe, graphite, or petroleum.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF THE PREFERRED EMBODIMENTS

According to the invention, there is provided a non-carcinogenic cream for topical application for delivery of active ingredients in the dermis of a patient for pain related to joint, lymphatic and blood circulation, nerve and skin.

The composition can be used in combination with an occlusive bandage.

It has been found that the non-carcinogenic cream for delivery of active ingredients in the dermis of a patient for treating pain, includes a synergistic combination of
about 10 to 25% of oil
about 10 to 25% of emulsifier
about 1 to 12% of preservative
about 45 to 80% of water, aloe water or hamamelis water; and
about 1 to 25% of at least one homeopathic active ingredient chosen from pancreatinum, ruta graveolens, ledum palustre, colchicum autumnale, symphytum officinalis, arnica montana, atropa belladonna, achillea millefolium, hamamelis, mercurius solubilis, mercurius iodatus, conium maculatum, echinacea angustifolia, echinacea purpurea, aconitum napellus, hypericum perforatum, bellis perennis, matricaria chamomilla, calendula officinalis, hepar sulphuris or a synergistic combination thereof.

Although greater amounts of the homeopathic active ingredient can be used in the composition it has been found that about 2 to 25% by weight of the combination of extracts is effective.

The compositions of the invention can be used in combination with other herbs or herbal extracts. For example, it may be desirable to thin the blood or to better promote circulation such as *Naja* and *Crotalus horridum*.

To condition the skin graphite and/or trace minerals such as copper and zinc salts may be included.

Other anti-inflammatory agents such as Lachesis Ninta that contains enzymes which relieves muscle tightness and cramps can be included in the composition.

The combinations as used herein stimulate the body's self healing mechanism by promoting circulation in the microcapillary system. This restores blood flow to the inflamed areas where most of the pain is realized. When blood flow is improved to an ailing joint, healing begins and true pain relief is realized.

The compositions of the invention may include other plant or herbal extracts. For example, there may be utilized extracts of Paraguay tea, Kola and Guarana which provide a source of methylxanthines, saponius, tannins and glycosides which have been shown to reduce swelling and redness. The extract of Paraguay tea is known as "Mate extract" and is described in the "International Cosmetic Ingredient Dictionary", 5th Edition. Mate extract is commercially available in combination with extracts of Kola and Guarana which is sold by Cosmetic Ingredient Resources of Stamford under the trademark "QUENCHT."

Suitable herbs which can be used also include *symphytum, officianalis, Moschus moscheferous*, Cow bezoar, *Pripalia geniculata, Plantago asiatica, Causticum, Helianthemum canadense, Ornithogalum umbellatum, Clematis crispa, Impatiens pallida, Prunus cerasus*, and the like.

The present invention will be more readily understood by referring to the following examples which are given to illustrate the invention rather than to limit its scope. The amounts indicated are by weight percent unless otherwise noted.

EXAMPLE 1

Cream to Treat Pain

A non-carcinogenic cream is prepared by admixing the following ingredients.
- 12.7% of a synergistic combination of emu oil, olive oil, argan nut oil, sunflower/safflower oil and coconut oil;
- 15.8% of a synergistic combination of oleyl oleate and cetearyl alcohol;
- 1.05% of a synergistic combination of glucose, glucose oxidase and lactoperoxidase;
- 65.67% of water and
- 4.78% of a combination of homeopathic extracts containing:
  - 0.05% by weight of pancreatinum,
  - 0.01% by weight of ruta graveolens,
  - 0.01% by weight of ledum palustre,
  - 0.1% by weight of colchicum autumnale,
  - 0.1% by weight of symphytum officinalis,
  - 1.5% by weight of arnica montana,
  - 0.5% by weight of atropa belladonna,
  - 0.07% by weight of achillea millefolium,
  - 0.45% by weight of hamamelis,
  - 0.04% by weight of mercurius solubilis,
  - 0.01% by weight of mercurius iodatus,
  - 0.1% by weight of conium maculatum,
  - 0.15% by weight of echinacea angustifolia,
  - 0.15% by weight of echinacea purpurea,
  - 0.5% by weight of aconitum napellus,
  - 0.09% by weight of hypericum perforatum,
  - 0.1% by weight of bellis perennis,
  - 0.15% by weight of matricaria chamomilla,
  - 0.45% by weight of calendula officinalis and
  - 0.25% by weight of hepar sulphuris.

EXAMPLE 2

Cream to Treat Pain

A non-carcinogenic cream is prepared by admixing the following ingredients.
- 14.7% of a synergistic combination of emu oil, olive oil, argan nut oil, sunflower/safflower oil and coconut oil;
- 12.8% of a synergistic combination of oleyl oleate and cetearyl alcohol;
- 1.05% of a synergistic combination of benzyl alcohol, salicylic acid, glycerin and sorbic acid;
- 65.67% of water and
- 4.78% of a combination of homeopathic extracts containing:
  - 0.05% by weight of pancreatinum,
  - 0.01% by weight of ruta graveolens,
  - 0.01% by weight of ledum palustre,
  - 0.1% by weight of colchicum autumnale,
  - 0.1% by weight of symphytum officinalis,
  - 1.5% by weight of arnica montana,
  - 0.5% by weight of atropa belladonna,
  - 0.07% by weight of achillea millefolium,
  - 0.45% by weight of hamamelis,
  - 0.04% by weight of mercurius solubilis,
  - 0.01% by weight of mercurius iodatus,
  - 0.1% by weight of conium maculatum,
  - 0.15% by weight of echinacea angustifolia,
  - 0.15% by weight of echinacea purpurea,
  - 0.5% by weight of aconitum napellus,
  - 0.09% by weight of hypericum perforatum,
  - 0.1% by weight of bellis perennis,
  - 0.15% by weight of matricaria chamomilla,
  - 0.45% by weight of calendula officinalis and
  - 0.25% by weight of hepar sulphuris.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method of using a non-carcinogenic cream for treating a condition in a subject, wherein said non-carcinogenic cream comprises:
   from 10% to 25% of oil;
   from 10% to 25% of emulsifier;
   from 1% to 12% of preservative;
   from 45% to 80% of water, aloe water or hamamelis water; and
   from 1% to 25% of a combination consisting of homeopathic extracts from ruta graveolens, ledum palustre, colchicum autumnale, symphytum officinalis, arnica montana, atropa belladonna, achillea millefolium, hamamelis, mercurius solubilis, mercurius iodatus, conium maculatum, echinacea angustifolia, echinacea purpurea, aconitum napellus, bellis perennis, matricaria chamomilla, hypericum perforatum, pancreatinum, calendula officinalis and hepar sulphuris;
   and wherein the condition is chosen from joints condition, blood circulation, lymphatic circulation, sensitive nerves, scars, keloids, and any combination thereof.

2. A non-carcinogenic cream for treating a condition in a subject, which comprises:
   from 12.7% to a maximum of 14.7% of oil;
   from 12.8% to a maximum of 15.8% of emulsifier;
   from 1% to 12% of preservative;
   a maximum of 65.67% of water, aloe water or hamamelis water; and
   4.78% of a combination of homeopathic extracts consisting of:
   0.01% by weight of ruta graveolens,
   0.01% by weight of ledum palustre,
   0.1% by weight of colchicum autumnale,
   0.1% by weight of symphytum officinalis,
   1.5% by weight of arnica montana,
   0.5% by weight of atropa belladonna,
   0.07% by weight of achillea millefolium,
   0.45% by weight of hamamelis,
   0.04% by weight of mercurius solubilis,
   0.01% by weight of mercurius iodatus,
   0.1% by weight of conium maculatum,
   0.15% by weight of echinacea angustifolia,
   0.15% by weight of echinacea purpurea, 0.5% by weight of aconitum napellus,
0.1% by weight of bellis perennis,
0.15% by weight of matricaria chamomilla,
0.09% by weight of hypericum perforatum,
0.05% by weight of pancreatinum,
0.45% by weight of calendula officinalis, and
0.25% by weight of hepar sulphuris;
and wherein the condition is chosen from joints condition, blood circulation, lymphatic circulation, sensitive nerves, scars, keloids, and any combination thereof.

3. A method for treating joints condition, blood circulation, lymphatic circulation, sensitive nerves, scars, keloids, and any combination thereof in a subject, the method comprising topically administering a therapeutically effective amount of the non-carcinogenic cream of claim 2 to the subject.

\* \* \* \* \*